United States Patent [19]
Favre et al.

[11] Patent Number: 5,955,602
[45] Date of Patent: *Sep. 21, 1999

[54] BRANCHED LACTOSE CONTAINING POLYSACHARIDES AND COMPOSITIONS CONTAINING THEM

[75] Inventors: Nicole Favre, Severy, Switzerland; Jérôme Lemoine, Lille, France; Jean-Richard Neeser, Savigny, Switzerland

[73] Assignee: Nestec S.A., Vevey, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/516,783

[22] Filed: Aug. 18, 1995

[30] Foreign Application Priority Data

Aug. 18, 1995 [EP] European Pat. Off. ............ 94870139

[51] Int. Cl.⁶ .................................................. C07G 17/00
[52] U.S. Cl. ...................... 536/123; 435/101; 435/252.9; 514/54; 424/485
[58] Field of Search ............................ 536/123; 435/101, 435/252.9; 424/485; 514/54

[56] References Cited

U.S. PATENT DOCUMENTS 4,396,763  8/1983  Tsuchiya et al. .

FOREIGN PATENT DOCUMENTS

B-26186/92   10/1992  Australia .
0 323 201 A2 12/1988  European Pat. Off. .
0 538 646 A1  9/1992  European Pat. Off. .
WO 87/06267   4/1997  WIPO .

OTHER PUBLICATIONS

Oda et al., Agric. Biol. Chem., (1983), 47(7) pp. 1623–1625.
Abstract of Japanese Patent Publication No. JP–A–05 039 304, published Feb. 19, 1993, obtained from the World Patents Index, Derwent Information Ltd., London, U.K. (Shigeo).
Yokoi, H., et al., "Isolation and Characterization of Polysaccharide–Producing Bacteria from Kefir Grains", *Journal of Dairy Science*, vol. 73, No. 7, pp. 1684–1689, Jul. 1990.
Toba, T., et al., "Comparative Study of Polysaccharides from Kefir Grains, an Encapsulated Homo–fermentative Lactobacillus Species and Lactobacillus Kefir", *Milchwissenschaft*, vol. 42, No. 9, pp. 565–568, 1987.
Yamamoto, Y., et al., "Structural Study on an Exocellular Polysaccharide Produced by *Lactobacillus helveticus* TY1–2", *Carbohydrate Research*, 261:67–78, 1994.

*Primary Examiner*—Irene Marx
*Attorney, Agent, or Firm*—Knobbe Martens Olson & Bear, LLP

[57] ABSTRACT

The present invention concerns a new branched natural soluble polysaccharide comprising a main chain having repeating side chains which are only made of lactose units, possibly substituted.

The present invention also concerns the microorganism by which this branched polysaccharide may be obtained and the food composition, the cosmetical composition and the pharmaceutical composition comprising said branched polysaccharide and/or microorganism.

11 Claims, 4 Drawing Sheets

BRANCHED LACTOSE CONTAINING POLYSACHARIDES AND COMPOSITIONS CONTAINING THEM

FIELD OF THE INVENTION

The present invention concerns a new branched polysaccharide, a microorganism producing it, the food composition, the pharmaceutical composition and the cosmetical composition containing them.

BACKGROUND OF THE INVENTION

Biological communication (the possibility for a cell to recognize a molecule or another cell) is a central phenomenon in pathological as well as in normal states.

Among the various mechanisms of molecular recognition between cells, and/or between cells and molecules, the binding of specific glycosidic structures by specialized proteins (lectins) is today considered as a major molecular recognition system.

The lectins may be bound specifically and non-covalently to well-defined glycosidic sequences.

Some lectins are bound, for example, to oligosaccharides which contain elevated mannose amounts, to structures carrying sialic acids, or to fucosylated glycosides.

Other lectins can bind β-galactosides and lactose.

Multigeneric coaggregations exist between oral bacterial cells (such as *Actinomyces naeslundii* or *viscosus, Streptococcus mitis* or *sanguis, Fusobacterium nucleatum, Porphyromonas gingivalis, Bacteriodes intermedius*, etc.) which aggregate and form a network as the dental plaque.

Between these bacterial cells, the interaction is often obtained by a non-covalent bond between a β-galactoside lectin on one cell and a glycosidic receptor on another cell (ref. 1).

Most infectious diseases are initiated by the adhesion of pathogenics agents (such as *Actinomyces naeslundii, Fusobacterium nucleatum, Bacteriodes intermedius, Salmonella typhimurium, Vibrio Cholera, Campylobacter jejuni, Bacteriodes, Fusobacteria, Clostridia, Shigella, Yersinia,* and *Helicobacter pylori*, etc.) to the epithelial cells of the mucosa of its host, which allows then the colonisation of the animal tissues.

This adhesion is often obtained by a binding between a β-galactoside lectin located at the surface of this pathogeneous agent and a glycosidic receptor located at the surface of the epithelial cell (ref. 2).

Various cells of the immune system (lymphocytes T and B. macrophages, neutrophils) are known either to be able to bind β-galactoside lectins or to express at their surface such lectins of the galectin family.

In addition, some epithelial cells such as intestinal cells or keratinocytes produce these galectins which can also coat Langerhans cells, and immunoglobulins such as IgE can specifically bind to galectins (ref. 3, 4 and 5).

STATE OF THE ART

There have been many prior studies upon polysaccharides produced by micro-organisms and, in recent years, there have been several reports of studies on the structure of exocellular polysaccharides obtained from lactic acid bacteria and on their biological activities.

A polysaccharide consisting of galactose, glucose and N-acetylgalactosamine (2:1:1) is obtained by the strains of *Streptococcus thermophilus* CNCM I-733, CNCM I-734 and CNCM I-735 (ref. 6 and 7);

a polysaccharide consisting of galactose only is obtained by the strain *Lactococcus cremoris* H414 (ref. 8);

a polysaccharide consisting of galactose, glucose, rhamnose and phosphate (2:2:1:1) is obtained by the strain *Lactococcus cremoris* SBT 0495 (ref. 9);

a polysaccharide consisting of galactose, glucose and rhamnose (5:1:1) is obtained by the strain *Lactobacillus bulgaricus* rr (ref. 10);

a polysaccharide consisting of glucose, rhamnose, 1-phosphoglycerol and a O-acetyl group (3:2:1:0.85) is obtained by the strain Lactobacillus sake 0-1 (ref. 11).

On the other hand, other polysaccharides obtained by a few strains of *Lactobacillus helveticus* were studied, but their structural characterization were never performed. For example, a polysaccharide of unknown structure consisting of glucose and galactose (2:1) used as an anti-tumor agent is obtained by the strain *Lactobacillus helveticus* var. *jugurti* No 851 "FERM BP-66 (FERM-P No 5851)" (ref. 12 and 13). Similarly, a polysaccharide of unknown structure consisting of galactose, glucose and N-acetylgluccsamine (2.5–3.5:2.5–3.5:1) used in treating inflammation and to accelerate bone marrow growth is obtained by the strain *Lactobacillus helveticus* MIKI-010 (ref. 14).

AIMS OF THE INVENTION

The present invention aims to provide a new branched polysacharide and/or the microorganism producing it, which can be used to inhibit the binding between β-galactoside lectins and their receptor(s).

Another aim of the invention is to provide food compositions comprising said polysaccharide and/or microorganism, having improved organoleptic and texture properties.

A further aim of the invention is to provide a pharmaceutical composition and/or cosmetical composition, comprising said polysaccharide and/or microorganism.

A last aim of the invention is to provide a polysaccharide which can be used as an intermediate product for the production of polymerized derivatives of gangliotriose, Sd-a blood group, or sialyl- and sulfated-Lewis X.

DESCRIPTION OF THE INVENTION

The present invention concerns a new natural soluble branched polysaccharide comprising a main chain having repeating side chains which are only made of lactose units, possibly substituted.

According to a preferred embodiment of the present invention, the branched polysaccharide corresponds to the following formula:

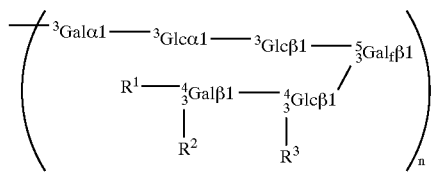

where n>1,
Gal=galactose,
Glc=glucose,
$R^1$=Hydrogen or GalNAcβ1 (N-acetylgalactosamine)
$R^2$=Hydrogen, NeuNAcα2 (N-acetylneuraminic Acid) or $HSO_3$
$R^3$=Hydrogen or Fucα1 (fucose)

When $R^1=R^2=R^3$=Hydrogen, the branched polysaccharide is characterized by the following physicochemical properties:
- molecular weight higher than 2,000,000, soluble in water and solutions containing less than 20% trichloroacetic acid,
- insoluble in alcohol and in acetone,
- neutral property,
- the freeze-dried product is in the form of white powder,
- component sugars and compositional ratio:Glucose:Galactose (1:1.1).

When $R^1$ is GalNAcβ1 (N-acetyl galactosamine) and $R^2=R^3$=Hydrogen, the branched polysaccharide is a derivative of the gangliotriose determinant which is advantageously obtained from an intermediate product (the polysaccharide with $R^1=R^2=R^3$=Hydrogen) by the methods described in documents 15 and 16.

When $R^1$ is GalNAcβ1 (N-acetyl galactosamine), $R^2$ is NeuNAcα2 (N-acetyl neuraminic Acid) and $R^3$ is Hydrogen, the branched polysaccharide is a derivative of the blood group Sd-a determinant, which is advantageously obtained from an intermediate product (the polysaccharide with $R^1=R^2=R^3$=Hydrogen) by the methods described in documents 17 and 18.

When $R^1$ is Hydrogen $R^2$ is NeuNAcα2 (N-acetylneuraminic Acid) or $HSO_3$ and $R^3$ is Fucα1 (fucose), the branched polysaccharide is a derivative of the pharmaceutical products sialyl- or sulfated- Lewis X described in documents 19 and 20.

The bindings between Gal β 1–4 Glc and $R^1$, $R^2$ are advantageously obtained from an intermediate product (the polysaccharide with $R^1=R^2=R^3$=Hydrogen) by the method described in document 17.

The present invention also concerns the microorganism producing the branched polysaccharide having $R^1=R^2=R^3$=Hydrogen.

Advantageously, said microorganism corresponds to a strain of *Lactobacillus helveticus*, preferably the strain of *Lactobacillus helveticus* CNCM I-1449.

A deposit of this microorganism has been made according to the Budapest Treaty on Jul. 27, 1994 under acession number CNCM I-1449, at the Collection Nationale de Culture de Microorganismes (CNCM), Institut Pasteur, 28 rue du Docteur Roux, 75724 PARIS CEDEX 15, FRANCE.

The present invention also concerns the food having improved organoleptic and texture properties comprising the polysaccharide and/or the microorganism according to the invention.

Preferably, said food composition is a set-style acidified milk or a stirred acidified milk.

Another aspect of the present invention concerns a cosmetic composition comprising the polysaccharide and/or the microorganism according to the invention.

According to a preferred embodiment of the invention, said cosmetic composition is a cosmetic product intended for buccal hygiene, choosen among the group consisting of a tooth paste, tooth gel, mouth rinse, chewing-gum and/or tablet.

According to another preferred embodiment of the present invention, said cosmetic composition is a product intended for skin hygiene, choosen among the group consisting of a cream, ointment or balsam.

Another aspect of the present invention concerns a pharmaceutical composition comprising the polysaccharide and/or the microorganism according to the present invention.

Advantageously, said composition is a antidiaorrheic product choosen among the group consisting of a capsule, syrup, powder and/or tablet.

A last aspect of the present invention concerns a diagnostic and/or analytic device comprising the branched polysaccharide according to the invention for the trapping of specific molecules and/or microorganisms.

DESCRIPTION OF A PREFERRED EMBODIMENT OF THE PRESENT INVENTION

Figure 1:
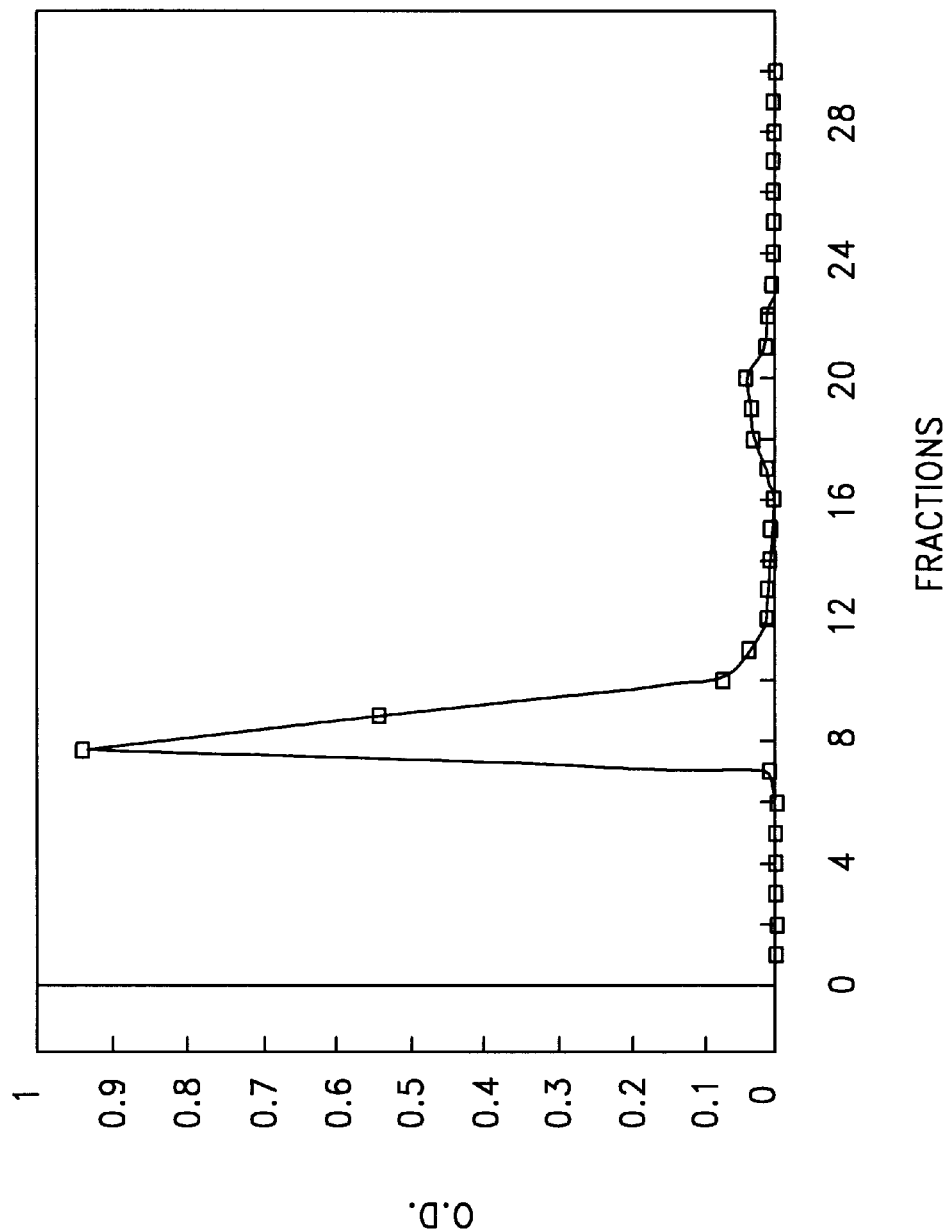
FIG. 1 represents the chromatographic (FPLC) analysis of the polysaccharide according to the invention.

The present invention concerns a new natural soluble branched polysaccharide with a main chain, having repeating side chains which are only lactose units, said lactose being possibly substituted.

The "branched polysaccharide" according to the invention is a saccharide having more than 10 repeating units, preferably more than 40 repeating units.

Said branched polysaccharide preferably has the structure of a "polymer" consisting of the repetition of identical single "units" comprising one side chain 2 branched on a main chain 1 as described below:

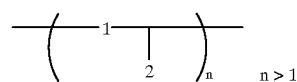

The production and the physico-chemical structure of a polysaccharide according to the invention will be described hereafter.

1. PREPARATION AND PURIFICATION OF THE EXOPOLYSACCHARIDE PRODUCED BY *LACTOBACILLUS HELVETICUS* CNCM I-1449

1.1 Fermentation Conditions.

*Lactobacillus helveticus* CNCM I-1449 was a ropy strain from the Nestlé strain collection. Among the 168 strains of *L. helveticus* of the Nestlé collection, only 2 strains produce exopolysaccharides.

The growth medium was 10% reconstituted skim milk heat-treated (115° C., 35 min) for sterilization prior to fermentation. A one-liter scale fermentor with a magnetic stirrer was used for regulating the pH during the fermentation. The pH was maintained at 5.5 by using 2N sodium hydroxide. Stirring rate was maintained at 60 RPM. Incubation was made at 40° C. The amount of starter culture inoculated to the medium was 1%. During the fermentation (time=6 h, 9 h and 24 h), several samples were taken and frozen for further analysis and polysaccharide extraction.

1.2. Extraction of the Polysaccharide.

An equal volume or trichlorcacetatic acid (40%) was added to the sample to remove proteins by precipitation, followed by centrifugation (17,000 g, 20 minutes). To the supernatant fraction containing polysaccharides, the same volume of acetone was added. Precipitated polysaccharides were then separated by centrifugation (17,000 g, 20 minutes).

The resulting precipitated fraction was dissolved in distilled water and pH was adjusted to 7.0 with sodium hydroxide solution. After dialysis against distilled water (overnight), insoluble substances were removed by ultracentrifugation (110,000 g, 1 hour).

The supernatant fraction containing polysaccharides was lyophilized and crude dehydrated polysaccharides were finally obtained. Total neutral sugar content was determined by the phenol-sulphuric acid method.

1.3. Size of the Exopolysaccharide.

Filtration was conducted to confirm purity and estimate the molecular weight of polysaccharides using FPLC system (Pharmacia). The column used was Superose 6 (1.0 cm×30 cm) (FIG. 1). 200 μl samples containing 200–400 μg dehydrated polysaccharides were applied on to the column, eluted with 50 mM phosphate buffer at pH 7.2 at the rate of 0.5 ml/min. Fractions (1.0 ml) were collected in tubes. Polysaccharide content in each tube was determined as total neutral sugar by the phenol-sulphuric acid method.

1.4. Monosaccharide Composition.

The monosaccharide composition of a freeze-dried polysaccharide was analyzed using gas-liquid chromatography technique (ref. 21).

The exopolysaccharide obtained from the spent culture medium was examined after extraction from three samples (time=6 h, 9 h and 24 h). The yield was found to increase as a function of the fermentation time, but the size as well as the monosaccharide composition of the polymer were found invariable:

| Fermentation Time | Crude Yield | Neutral Sugars | Pure Yield | Monosaccharide Composition | | | |
|---|---|---|---|---|---|---|---|
| (hours) | (mg/L) | (%) | (mg/L) | Rha | Gal | Glc | GalNAc |
| 6 | 42 | 27.6 | 11.6 | — | 1.1 | 1 | — |
| 9 | 142 | 70.4 | 100.0 | — | 1.1 | 1 | — |
| 24 | 272 | 83.3 | 226.6 | — | 1.1 | 1 | — |

FIG. 1 shows the elution and the purity of the polysaccharide obtained at t=24 h, by FPLC analysis (with a column of Superose 6). The polysaccharide was eluated at around the exclusion limit (approximately $2 \times 10^6$ M.W.)

1.5. Yields of Polysaccharide Obtained in Non-Regulated Fermentations.

The polysaccharide described above was also produced during fermentations in set-style conditions, by *Lactobacillus helveticus* CNCM I-1449 alone, or by this strain used together with a strain of *Streptococcus thermophilus* (for example *S. thermophilus* YS4).

For this purpose, the growth medium was 10% reconstituted MSK (skim milk powder: 100 g/l and yeast extract: 1 g/l) heat-treated (115° C., 35 min) for sterilization prior to fermentation. The typical sample size was 250 ml, the incubation was made at 40° C. and the amount of starter culture inoculated to the medium was 1%. The yields of pure polysaccharide obtained in such conditions were the following:

| Strains in the Starter Culture | Fermentation Time (hours) | Pure Yield (mg/l) |
|---|---|---|
| *L. helveticus* CNCM I-1449 | 8 | 85 |
| | 16 | 140 |
| *L. helveticus* CNCM I-1449 & *S. thermophilus* YS4 | 4 | 23 |
| | 8 | 81 |

2. METHODS USED FOR THE STRUCTURAL CHARACTERIZATION OF THE EXOPOLYSACCHARIDE PRODUCED BY *LACTOBACILLUS HELVETICUS* CNCM I-1449.

2.1. Monosaccharide Analysis.

Polysaccharide (0.1 mg) was methanolysed (methanolic 0.5 M HCl, 24 h, 80° C.) and (one night at room temperature). The trimethylsilylated methyl glycosides were analysed by gas phase chromatography (Varian 3400) using a BP1 fused-silica capillary column (25 m×0.32 mm, SGE). The elution was performed by applying on the column a temperature gradient from 120° C. to 240° C. at 2° C. $\min^1$. The absolute configuration of the monosaccharides was determined by GLC of the trimethylsilylated (N-reacetylated) (−)-2-butyl glyclosides.

2.2 Methylation Analysis.

Samples (native polysaccharide and oligosaccharide-alditols) were permethylated, and methylated products were subjected either to methanolysis or acid hydrolysis (trifluoroacetic acid 4N, 4 h, 100° C.) followed by reduction with $BD_4Na$.

The partially methylated and acetylated (pyridine anhydride acetic 1:1) methyl glycosides and alditols were identified by GLC (BP1 column) and GLC MS in e.i. mode on a Nermag R10-10S mass spectrometer using an electron energy of 70 ev and an ionizing current of 0.2 mA.

2.3. Partial Acid Hydrolysis.

Polysaccharide (40 mg) was hydrolysed in 4 ml of 0.5 M trifluoroacetic acid during 1 h 30 at 100° C. Complete hydrolysis and obtention of low mass oligosaccharides were monitored by thin layer chromatography on Silica Gel 60 F254 aluminium sheets (Merck) using a butanol/water/acetic acid 2:1:1.5 solvent and detection with orcinol-sulfuric acid.

2.4. H.p.a.e-p.a.d. Chromatography.

Fractionation of HW40 peaks was performed on HPAE-PAD Dionex LC system consisting of a Dionex Bio-LC quaternary gradient module, a model p.a.d. 2 detector and a Carbopac PA-1 pellicular anion exchange column (250×9 mm).

Two elution programs were used:

program 1: 99:1 eluent A (0.1 M NaOH)—eluent B (0.1 M NaOH containing M $CH_3COONa$) for 0.2 min then going to 65:35 eluent A (0.1 M NaOH containing M $CH_3COONa$) in 60 min at 3 ml $min^{-1}$;

program 2: 98:2 eluent A—eluent B then going to 70:30 eluent A—eluent B in 60 min.

The eluted fractions were immediately neutralized with M acetic and lyophilized. The fractions were successively desalted on a column (6×1 cm) of Dowex 50×8 (H') resin and on a column of Fractogel (55×2 cm) using deionised water as eluent.

2.5. $^1$H-Nuclear Magnetic Resonnance Spectroscopy.

For $^1$H-NMR measurements, the deuterium-exchanged oligosaccharides were dissolved in 0.5 ml of $^2H_2O$ (99.96% atom $^2$H, Aldrich). The 400 MHz $^1$H-NMR experiments were performed with a Bruker AM-400WB spectrometer, equipped with a 5 mm $^1$H-/$^{13}$C mixed probe head, operating in the pulsed Fourier transform mode and controlled by an Aspect 3000 computer.

All the spectra were obtained at a probe temperature of 353° K. One dimensional spectra were obtained with a spectral width of 3000 Hz for a 16K frequency-domain points and time-domain data points giving a final digital resolution of 0.365 Hz/point.

The 100 MHz $^{13}$C-NMR experiments were obtained with the standard Brucker pulse program Powgate with $^1$H composite pulse decoupling. The spectral width was 22.727 Hz for a 32K frequency-domain data points and time-domain data giving a final digital resolution of 1.387 Hz/point; a ninety-degree pulse (6 $\mu$s) and 1 s recycle delay were used. The chemical given relative to the signal of the methyl group of acetone ($\delta$ 2.225 for $^1$H and $\delta$ 31.55 for $^{13}$C).

The 2D-homonuclear COSY 45, COSY with simple, double-and triple relay transferts were performed by use of the standard Bruker pulse program library or the programs given by B. Perly (C.E.A., Saclay). For all RCT experiments, refocusing delays of 35 ms were chosen and the relaxation delay was 2 s. In all these experiments, the spectral width was 1840 Hz, the $^1$H ninety-degree pulse was 10.6 $\mu$s; 256 W×2K data matrices were acquired, which were zero-filled prior to Fourier transform, to obtain a 1K×2K spectral data matrix and a sine-bell squared function was used in both dimensions.

The 2D-$^{13}$C/$^1$H COSY experiments were performed with simultaneous suppression of $^1$H homonuclear couplings by use of the standard Bruker pulse program XHCORRD. Refocusing delays were adjusted to an average $^1j_{C,H}$ coupling constant of 150 KHz. $^1$H and $^{13}$C ninety-degree pulse width were 10.6 and 6 $\mu$s. The relaxation delay was 0.8 s. 128 W×4K data matrix was acquired, which was zero-filled prior to Fourier transform, to obtain a 512 W×4K spectral data matrix. An exponential function (LB=1 Hz) for $^{13}$C-subspectra and a sine-bell function for $^1$H-spectra were applied to enhance the signal to noise ratio.

3. STRUCTURE OF THE EXOPOLYSACCHARIDE PRODUCED BY *LACTOBACILLUS HELVETICUS* CNCM I-1449.

3.1. Isolation and Composition Analysis of the Polysaccharide.

GLC. analysis of the trimethylsilylated glycosides and (−)-2-butyl glyosides has confirmed the presence of D-galactose and D-glucose in a molar ratio 1:1.

NMR spectroscopy.

The 400 MHz $^1$H n.m.r. spectrum of the native polysaccharide recorded in $D_2O$ at 80° C. shows 4 signals at 5.201, 5.158, 4.568 and 4.350 ppm characteristic of anomeric protons in a ratio 1:2:2:1 suggesting a hexasaccharide repeating unit (table 1).

This is confirmed by the 100 MHz $^{13}$C spectrum (table 1) that exhibits six anomeric carbon signals (108.95, 103.74, 103.8, 102.52, 100.26 and 99.87 ppm).

According to the $^1$H spin system, on individual sugar units depicted on the two setaps relayed COSY sprectrum, the monosaccharides may be respectively identified as β-$Gal_f$ (residue A), β-D-$Glc_p$ (residues B and E), α-D-$Glc_p$ (residue C), α-D-$Gal_p$ (residue D) and β-D-$Gal_p$ (residue F)

Examination of the relayed COSY spectra of oligosaccharide alditols IV B and II A obtained by partial acid hydrolysis (see below) leads to the obvious identification of the β-D-$Gal_p$. As demonstrated by the COSY spectrum of the polysaccharide, the H-2 and H-3 of the β-D-$Gal_p$ F residue exhibit a strong coupling constant which does not allow an to analysis of their multiple patterns.

Correlation peaks observed in the $^1$H-$^{13}$C heteronuclear COSY spectrum show that one of the proton resonances (5.158 ppm) is connected to the carbon resonance deshielded at 108.95 ppm that proves a β-anomeric configuration for the $Gal_f$ A residue.

Most of the proton resonances may be assigned in the homonuclear COSY spectrum except for the H-5 and H-6 spin systems of the β-D-$Gal_p$ F residue. The carbon resonances may also be assigned by direct correlation to their attached protons.

The two remaining unassigned carbons at 73.52 and 61.12 ppm were deduced to correspond with the C-5 and C-6 atom resonances of β-D-$Gal_p$ F residue.

In summary, all these-assignments clearly furnish the substitution pattern of each sugar unit, according to their downfield shifted carbon resonances:

C-3 and C-5 for β-D-$Gal_f$ A,

C-3 for α-D-$Glc_p$ C,

C-3 for α-D-$Gal_p$ D,

C-3 for β-D-$Glc_p$ B and

C-4 for β-D-$Glc_p$ E.

The sixth sugar unit β-D-$Gal_p$ F, which does not possess any downfield shifted $^{13}$C resonance, occurs consequently in a non-reducing position.

3.2. Methylation Analysis.

The NMR results are supported and confirmed by GLC MS analysis of the partially methylated alditol acetates and methyl glycosides (Table 2) obtained from the permethylated polysaccharides. Indeed, it demonstrates the presence of terminal galactosyl residue, 3-linked glucosyl residue, 4-linked glucosyl residue, 3-linked galactosyl residue and 3,5 linked galactosyl residue in a ratio 1:2:1:1:1 respectively.

3.3. Partial Acid Hydrolysis.

Figure 2:
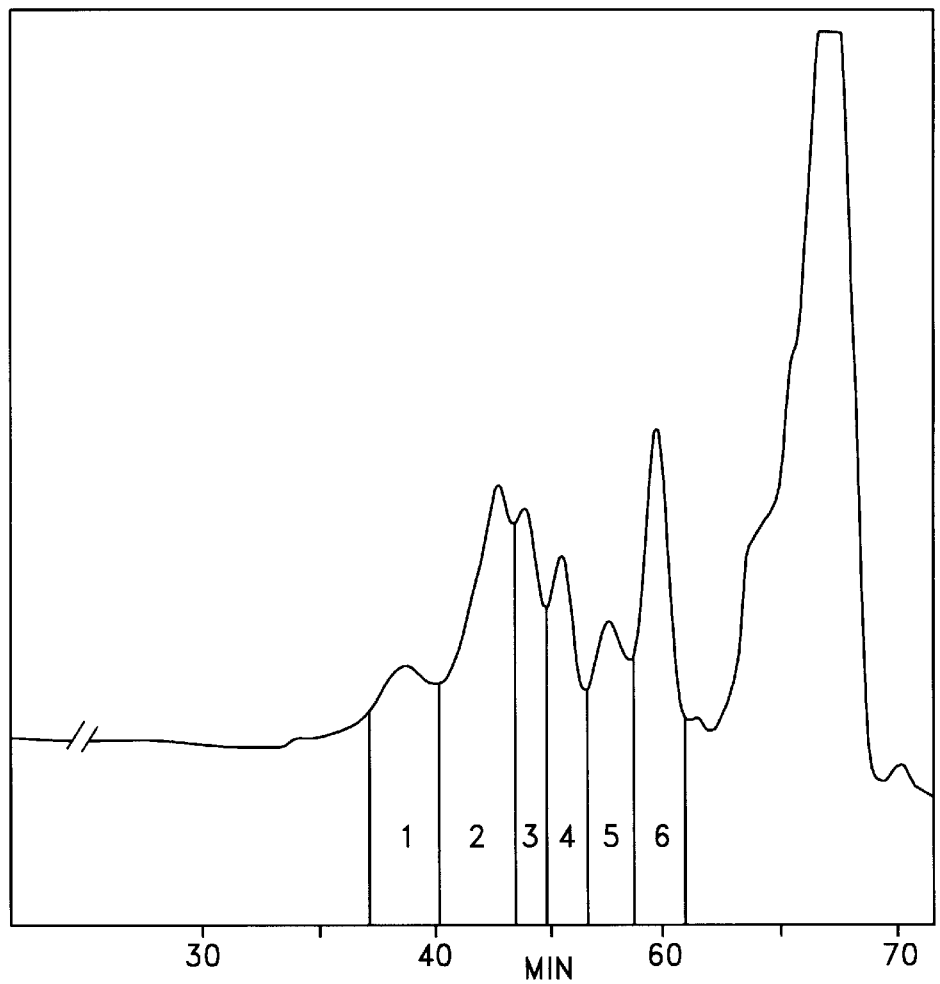
FIG. 2 represents six major fractions separated by gel filtration from the polysaccharide hydrolysate.

In order to elucidate the position of the branched terminal galactosyl residue, oligosaccharides were produced by partial acid hydrolysis of the native polysaccharide. Six major fractions were separated by gel filtration on Fractogel HW40 F from the hydrolysate (FIG. 2).

Figure 3:
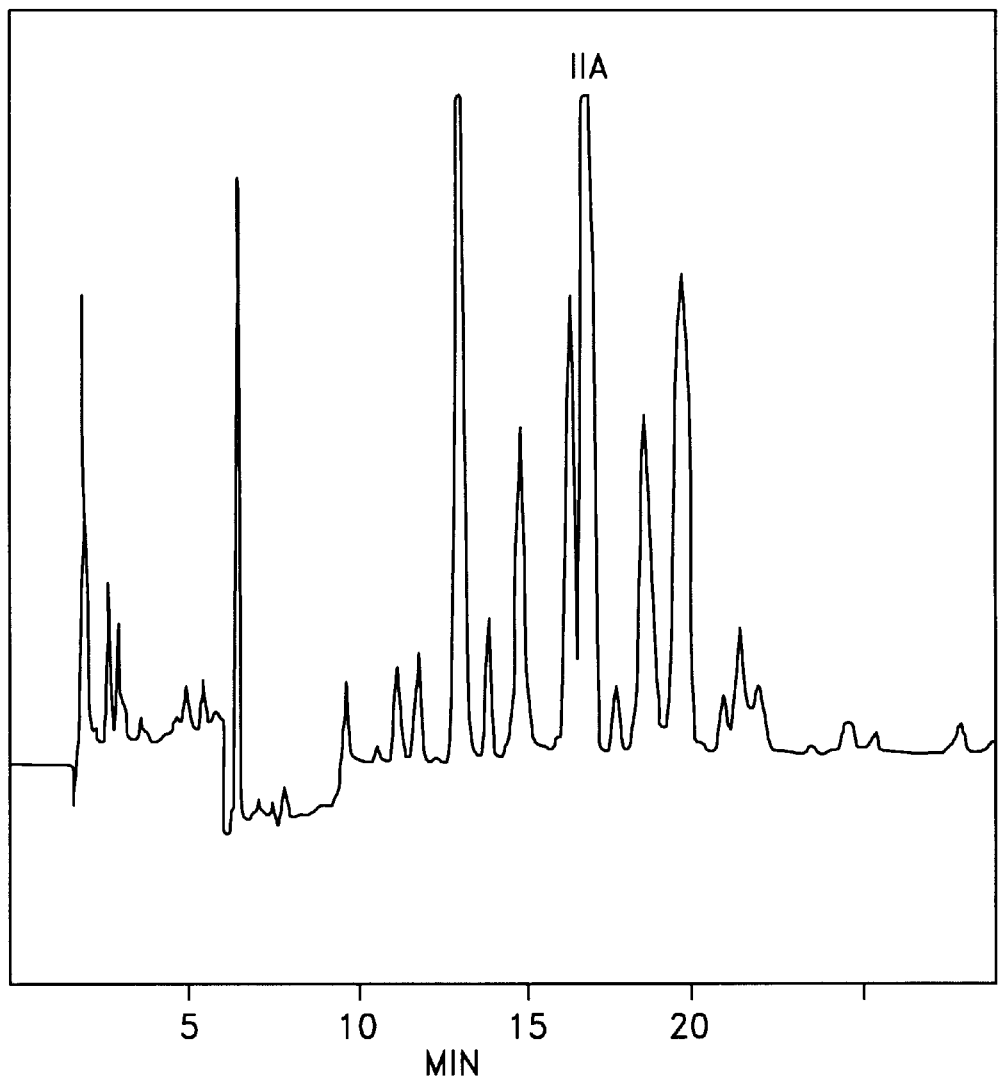
FIG. 3 represents the chromatographic (HPAE-PAD) analysis of fraction II.
Figure 4:
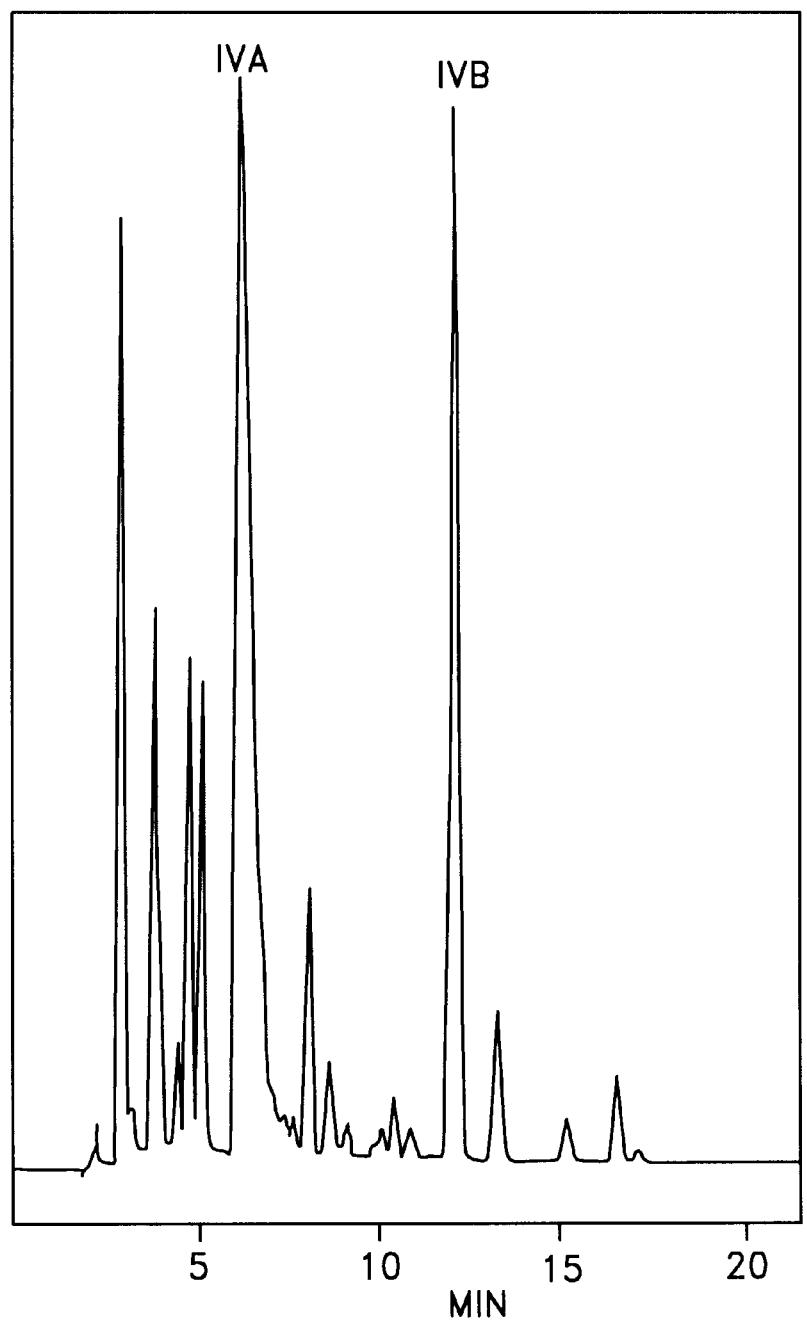
FIG. 4 represents the chromatographic (HPAE-PAD) analysis of fraction IV.

Two of them (fractions II and IV) were subjected to HPAE-PAD chromatography (FIG. 3, 4 and table 3) and the structure of subfractions denoted II A, IV A and IV B was investigated both by NMR and methylation analysis.

Oligosaccharide-alditol IV A contains two Glc residues and one hexitol residue, as shown by the $^1$H spin system depicted in the two-steps relayed COSY spectrum. The two Glc residues occur at the non-reducing terminal position, as confirmed by the methylation analysis which furnished 2, 3, 4, 6-tetra-O-methyl glucitol. The last derivative shows a pattern corresponding to a C-3 and C-5 substitution characteristic of a furanic sugar. From the previous n.m.r. data, this hexitol originates from the β-D-Gal$_f$ A unit. These findings lead to the following structure:

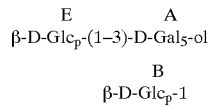

It must be noted that due to the symmetry displayed by the $^1$H spin system of galactitol, the $^1$H NMR assignment of the compound was achieved after the elucidation of compound IV B structure.

Oligosaccharide-alditol IV B contains β-D-Gal$_p$ and β-D-Glc$_p$ in the ratio 1:1, as clearly shown by the pattern of the vicinal coupling constants. The methylation analysis (Table 4) indicated the presence of 2, 3, 4, 6-tetra-O-methyl galactose, 2, 3, 6-tri-O-methyl glucose and 1, 2, 4, 5, 6-penta-O-methyl galacticol. Therefore, oligosaccharide-alditol 2 possesses the following structure:

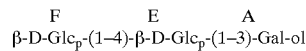

The attachment of β-D-Glc$_p$ at C-3 of Gal-ol is not susceptible to modify dramatically the chemical shift of the H-1 and H-2 resonances of the hexitol, when compared with the NMR data from compound IV A. Therefore, the two signals at 3.77 and 4.056 ppm can be assigned to H-1 and H-2 of Gal-ol, whereas the H-5 and H-6 atoms resonances are upfield shifted at 4.149 and 3.68 ppm, by comparison with commpound IV A (Table 3).

In the NMR spectra of IV A and IV B, the H-5 resonance of Gal-ol is the most upfield shifted atom resonance of the molecule and this observation is in agreement with the assignments proposed by others.

Oligosaccharide-alditol II A (Table 2) contains 2 β-D-Glc$_p$, 1 β-D-Gal$_p$ and 1 α-D-Glc$_p$ residues, whereas the presence of C-3 and C-5 substituted Gal-ol can be easily deduced by the similarity in chemical shifts of H-1 to H-6 of Gal-ol in compound 1. Since the two β-D-Glc$_p$ units and the non-reducing terminal β-D-Gal$_p$ have already been located in oligosaccharide-alditols IV A and IV B, and according to the fact that the β-D-Glc$_p$ B residue is C-3 substituted, the oligosaccharide-alditol II A possesses the following structure:

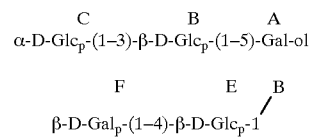

The sixth sugar unit, α-D-Gal$_p$, was not observed among the products of the partial hydrolysis. Nevertheless, the fact that the α-D-Glc$_p$ unit C is C-3 substituted and that the only β-D-Gal$_p$ present in the polysaccharide occupies the non-reducing position (from the NMR data) lead us to conclude that the α-D-Gal$_p$ is attached to this α-D-Glc$_p$ residue.

Therefore, the structural unit of the polysaccharide was defined as follows:

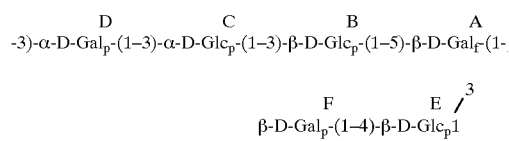

TABLE 1

NMR chemical shift of the polysaccharide from in D$_2$O at 80° C. (internal standard: acetone)

| | Residue | | | | | |
|---|---|---|---|---|---|---|
| Assignment | β-Gal$_p$ A | β-Glc$_p$ B | α-Glc$_p$ C | α-Gal$_p$ D | β-Glc$_p$ E | β-Gal$_p$ F |
| $^1$H (ppm) | | | | | | |
| H-1 | 5.158 | 4.568 | 5.201 | 5.158 | 4.568 | 4.350 |
| H-2 | 4.240 | 3.289 | 3.542 | 3.888 | 3.206 | 3.470 |
| H-3 | 4.419 | 3.532 | 3.752 | 3.776 | 3.488 | 3.470 |
| H-4 | 4.125 | 3.533 | 3.512 | 3.999 | 3.533 | 3.796 |
| H-5 | 4.118 | 3.354 | 3.920 | 4.108 | 3.455 | 3.582 |
| H-6 | 3.723 | 3.84 | 3.61 | 3.62 | 3.90 | 3.67 |
| H-6' | 3.62 | 3.66 | 3.61 | 3.62 | 3.70 | 3.67 |
| $^{13}$C (ppm) | | | | | | |
| C-1 | 108.95 | 103.08 | 99.87 | 100.26 | 102.52 | 103.74 |
| C-2 | 80.52 | 72.72 | 71.19 | 68.33 | 73.47 | 71.19 |
| C-3 | 85.08 | 85.15 | 82.90 | 77.31 | 74.90 | 75.32 |
| C-4 | 81.64 | 70.14 | 70.20 | 69.19 | 80.19 | 68.69 |
| C-5 | 78.84 | 76.43 | 72.48 | 71.27 | 73.52 | 75.80 |
| C-6 | 61.68 | 61.38 | 61.07 | 61.26 | 61.12 | 60.99 |

TABLE 2

Methylation analysis of the native polysaccharide

| | molar ratio | |
|---|---|---|
| derivative | partially methylated alditol-acetates | partially methylated methylglycosides |
| 2, 3, 4, 6 Gal | 1 | 1 |
| 2, 4, 6 Glc | 22 | 19 |
| 2, 3, 6 Glc | 9 | 13 |
| 2, 4, 6 Gal | 7 | 16 |
| 2, 6 Gal | 1 | 9 |

TABLE 3

NMR chemical shifts of the oligosaccharide-alditols obtained by acid partial hydrolysis of the polysaccharide from *Lactobacillus helveticus* in D2O at 353° K.

| | Residue in IV A | | | Residue in IV B | | | Residue in II A | | | | |
|---|---|---|---|---|---|---|---|---|---|---|---|
| assignment $^1$H (ppm) | Gal-ol A-ol | $\mu$-Glc$_p$ E | $\beta$-Gal$_p$ F | Gal-ol A-ol | $\beta$-Glc$_p$ B | $\beta$-Glc$_p$ E | Gal-ol A | $\beta$-Glc$_p$ B | $\beta$-Glc$_p$ C | $\beta$-Glc$_p$ D | $\beta$-Gal$_p$ E |
| H-1 | 3.77 | 4.686 | 4.557 | 3.77 | 4.539 | 4.428 | 3.77 | 4.707 | 5.340 | 4.590 | 4.460 |
| H-1' | 3.77 | — | — | 3.77 | — | — | 3.77 | — | — | — | — |
| H-2 | 4.118 | 3.328 | 3.320 | 4.056 | 3.421 | 3.541 | 4.120 | 3.423 | 3.559 | 3.379 | 3.542 |
| H-3 | 4.141 | 3.500 | 3.484 | 3.915 | 3.661 | 3.661 | 4.148 | 3.647 | 3.748 | 3.647 | 3.665 |
| H-4 | 3.907 | 3.424 | 3.406 | 3.797 | 3.674 | 3.927 | 3.911 | 3.748 | 3.463 | 3.678 | 3.928 |
| H-5 | 4.301 | 3.543 | 3.453 | 4.149 | 3.62 | 3.732 | 4.299 | 3.47 | 4.025 | 3.590 | 3.73 |
| H-6 | 3.77 | 3.899 | 3.899 | 3.68 | 4.02 | 3.79 | 3.77 | 3.97 | 3.80 | 3.90 | 3.79 |
| H-6' | 3.77 | 3.758 | 3.758 | 3.68 | 3.80 | 3.79 | 3.77 | 3.85 | 3.80 | 3.75 | 3.79 |

TABLE 4

Methylation analysis of oligosaccharide-alditol (partially methylated and acetylated methyl glycosides) IV A, IV B and II A obtained by partial acid hydrolysis of native polysaccharide.

| | molar ratio | | |
|---|---|---|---|
| derivative | IV A | IV B | II A |
| 1, 2, 4, 5, 6 Gal-ol | — | 1 | — |
| 1, 2, 4, 6 Gal-ol | 1 | — | 1 |
| 2, 3, 4, 6 Glc | 1.2 | — | 1.0 |
| 2, 3, 4, 6 Gal (*) | — | 1.4 | 0.9 |
| 2, 4, 6 Glc | — | — | 1.3 |
| 2, 3, 6 Glc | — | 1.0 | 1.2 |

(*): Due to its high volatility the value is lower than expected.

The compositions comprising the polysaccharide and/or microorganism according to the invention are described in the following non limiting examples.

EXAMPLE 1
Set-Style Acidified Milk.

Set-style acidifed milk comprising the *L. helveticus* strain according to the invention and two *S. thermophilus* strains, traditionnaly used for the production of a set-style yoghourt, was obtained by the following process.

To a whole milk comprising 3.7% fats, 2.5% skimmed milk powder was added.

40 liters of this milk was pasteurized at 92° C. for six minutes, homogeneized at 75° C. and 150 bars (two levels) and cooled at a temperature around 42° C.

The freeze-dried *S. thermophilus* CNCM I-1422, *S. thermophilus* CNCM I-1424 and *L. helveticus* CNCM I-1449 strains were reactived with several successive cultures in a sterile MSK medium (skimmed milk powder reconstituted at 10%, comprising 0,1% of a commercial yeast extract).

A deposit of the microorganism has been made according to the Budapest Treaty on May 18, 1994, for the Streptococcus strains and on Jul. 27, 1994, for the Lactobacillus strain at the Collection Nationale de Culture de Microorganismes (CNCM), Institut Pasteur, 28 rue du Docteur Roux, 75724 PARIS CEDEX 15, FRANCE.

The sterilized milk was inoculated with 1% of the third culture of each *S. thermophilus* strain and with 2% of the second culture of *L. helveticus* strain taken at the medium coagulation stage.

The milk was incubated at 42° C. and at a pH around 4.65, and then cooled at a temperature of 4° C.

EXAMPLE 2
Acidified Whey Milk.

Whey milk comprising the *L. helveticus* strain according to the invention and two *S. thermophilus* strains, traditionnaly used for the production of a yoghourt, was obtained by the following process.

A sweet lactoserum powder was reconstituted at 12.5% in water.

40 liters of this whey was pasteurized at 92° C. for six minutes, homogeneized at 75° C. and 150 bars (two levels) and cooled at a temperature around 42° C.

The freeze-dried *S. thermophilus* CNCM I-1422, *S. thermophilus* CNCM I-1424 and *L. helveticus* CNCM I-1449 strains were reactived with several successive cultures in a sterile MSK medium (skimmed milk powder reconstituted at 10%, comprising 0.1% of a commercial yeast extract).

A deposit of the microorganism has been made according to the Budapest Treaty on May 18, 1994, for the Streptococcus strains and on Jul. 27, 1994, for the Lactobacillus strain at the Collection Nationale de Culture de Microorganismes (CNCM), Institut Pasteur, 28 rue du Docteur Roux, 75724 PARIS CEDEX 15, FRANCE.

The sterilized milk was inoculated with 1% of the third culture of each *S. thermophilus* strain and with 2% of the second culture of *L. helveticus* strain taken at the medium coagulation stage.

The whey milk was incubated at 42° C. and at a pH around 4.65, and then cooled at a temperature of 4° C.

EXAMPLE 3
Stirred Acidified Milk.

A stirred acidifed milk comprising the *L. helveticus* CNCM I-1449 strain according to the invention and two commercialized *S. thermophilus* strains, traditionnaly used for the production of a stirred yoghourt, was obtained by the following process.

The milk was obtained from a whole milk comprising 3.7% fats, by the addition of 2.5% skimmed milk powder.

40 liters of this milk was pasteurized at 105° C. for two minutes, homogeneized at 75° C. and 300 bars (first level) and cooled at a temperature around 43° C.

The lyophilized *S. thermophilus* CNCM I-1421, *S. thermophilus* CNCM I-1423 and *L. helveticus* CNCM I-1449 strains were reactivated with several successive cultures in a sterile MSK medium.

A deposit of the microorganism has been made according to the Budapest Treaty on May 18, 1994, for the Streptococcus strains and on Jul. 27, 1994, for the Lactobacillus strain at the Collection Nationale de Culture de Microorganismes (CNCM), Institut Pasteur, 28 rue du Docteur Roux, 75724 PARIS CEDEX 15, FRANCE.

The sterilized milk was inoculated with 1% of the third culture of each *S. thermophilus* strain and with 2% of the third culture of *L. helveticus* strain taken at the medium coagulation stage.

The milk was incubated at 43° C. and at a pH around 4.65, and then cooled at a temperature of 4° C. during stirring.

The following table 5 represents the properties of the obtained products.

TABLE 5

|  | Example 1 | Example 3 |
|---|---|---|
| Acidification time at pH = 4.65 | 6 h | 7 h 15 |
| pH of the product after 1 day at 4° C. | 4.34 | 4.49 |
| pH of the product after 24 days at 4° C. | 4.1 | 4.3 |
| taste after 24 days | good taste, slightly acid smooth texture | very good taste, aromatic smooth and onctuous texture |

EXAMPLE 4

Cosmetic Composition for Buccal Hygiene.

| CHEMICAL NAME | TRADE NAME | % WEIGHT |
|---|---|---|
| PHASE A | | |
| PEG-40 Hydrogenated castor oil | Cremophor RH 40 | 0.10 |
| Flavour | Strawberry E 2226 | 0.04 |
| Flavour | Raspberry 9/022436 | 0.10 |
| PHASE B | | |
| Sodium Cyclamate | Sodium Cyclamate | 0.10 |
| Exopolysaccharide according to the present invention | — | 0.50–5.00 |
| Demineralized water | — | 94.66–99.16 |
| TOTAL | | 100 |

EXAMPLE 5

Cosmetic Composition for Skin hygiene.

| | | % WEIGHT |
|---|---|---|
| OIL PHASE | | |
| | BRIJ 721 (Steareth 21) | 4.00 |
| | Cetyl alcohol | 10.00 |
| | Mineral oil | 5.00 |
| | Propyl parahydroxybenzoate | 0.02 |
| WATER PHASE | | |
| | CARBOPOL 934 (Carbomer 934) | 0.10 |
| | Sodium hydroxide (solution at 10%) | 0.10 |
| | Methyl parahydroxybenzoate | 0.18 |
| | Exopolysaccharide according to the present invention | 0.50–5.00 |
| | Demineralized water | 75.60–80.10 |
| | TOTAL | 100 |

EXAMPLE 6

Pharmaceutical composition for anti-diarrheoic usage.

A pharmaceutical composition was obtained as a capsule which was made with gelatine and water, and which contained from 5 to 50 mg of the exopolysaccharide according to the present invention. Alternatively, powdered tablet formulations can be obtained directly from the acidified cultured milks described in the above examples 1, 2 and 3, by freeze-drying these fermented milks and whey.

References

1. Kolenbrander, P. E., Ganeshkumar, N., Cassels, F. J. & Hughes, C. V., Coaggregation: specific adherence among human oral plaque bacteria. *The FASEB Journal*, 7 (1993) 406–413.
2. Karlsson, K.-A., Animal glycosphingolipids as membrane attachment sites for bacteria. *Annual Review of Biochemistry*, 58 (1989) 309–350.
3. Hughes, R. C., Mac-2: A versatile galactose-binding protein of mammalian tissues. *Glycobiology*, 4 (1994) 5–12.
4. Truong, M.-J., Gruart, V., Kusnierz, J.-P., Papin, J.-P., Loiseau, S., Capron, A. & Capron, M., Human neutrophils express immunoglobulin E (IgE)-binding proteins (Mac-2/εBP) of the S-type lectin family: role in IgE-dependent activation. *Journal of Experimental Medicine*, 177 (1993) 243–248.
5. Wollenberg, A., de la Salle, H., Hanau, D., Liu, F.-T. & Bieber, T., Human keratinocytes release the endogenous β-galactoside-binding soluble lectin immunoglobulin E (IgE-binding protein) which binds to Langerhans cells where it modulates their binding capacity for IgE glycoforms. *Journal of Experimental Medicine*, 178 (1993) 777–785.
6. Doco, T., Fournet, B., Carcano, D., Ramos, P., Loones, A., Piot, J.-M. & Guillochon, D., Polysaccharide, application comme agent épaississant et comme agent anti-tumoral. *Demande de brevet européen*, EUR 331 564, 06.09.1989.
7. Doco, T., Wieruszeski, J.-M., Fournet, B., Carcano, D., Ramos, P. & Loones, A., Structure of an exocellular polysaccharide produced by *Streptococcus thermophilus*. *Carbohydrate Research*, 198 (1990) 313–321.
8. Gruter, M., Leeflang, B. R., Kuiper, J., Kamerling, J. P. & Vliegenthart, J. F. G., Structure of the exopolysaccharide produced by *Lactococcus lactis* subspecies cremoris H414 grown in a defined medium or skimmed milk. *Carbohydrate Research*, 231 (1992) 273–291.
9. Nakajima, H., Hirota, T, Toba, T., Itoh, T. & Adachi, S., Structure of the extracellular polysaccharide from slime-forming *Lactococcus lactis* subsp. cremoris SBT 0495. *Carbohydrate Research*, 224 (1992) 245–253.
10. Gruter, M., Leeflang, B. R., Kuiper, J., Kamerling, J. P. & Vliegenthart, J. F. G., Structural characterization of the exopolysaccharide produced by *Lactobacillus delbrückii* subspecies bulgaricus rr grown in skimmed milk. *Carbohydrate Research*, 239 (1993) 209–226.
11. Van den Berg, D. J. C., Ledeboer, A. M., Robijn, G. W. & Vreeker, R., Lactobacillus sake like strains, production and use of their exopolysaccharides. International Patent Application PCT No WO 94/12656, Jun. 9, 1994.
12. Tsuchiya, F., Miyazawa, K., Kanbe, M., Oda, M. & Ebisawa, N., High molecular polysaccharide MPS-80. U.S. Pat. No. 4,396,763, Aug. 2, 1983.
13. Oda, M., Hasegawa, H., Komatsu, S., Kambe, M. & Tsuchiya, F., Anti-tumor polysaccharide from Lactobacillus sp. *Agricultural and Biological Chemistry*, 47 (1983) 1623–1625.
14. Yamamoto, Y., Polysaccharide NPS, method for making it and uses thereof. Laid-open patent application from the Japanese Patent Office No 5-186501, Jul. 27, 1993.
15. Lutz M. S, Jaskiewica E., Darling D. S., Furukawa K., Young W. W. Jr., Cloned beta-1, 4 N-acetylgalactosaminyltransferase synthesizes G-A2 as well as gangliosides G-M2 and G-D2: G-M3 synthesis has priority over G-A2 synthesis for utilization of lactosylceramide substrate in vivo. *Journal of Biological Chemistry*, 269 (1994) 29227–29231.
16. Yamashiro S., Haraguchi M., Furukawa K., Takamiya K., Yamamoto A., Nagata Y., Lloyd K. O., Shiku H., Furukawa K., Substrate specificity of beta-1,4-N-acetylgalactosaminyltransferase in vitro and in cDNA transfected cells: G-M2-G-D2 synthase efficiently generates asialo-G-M2 in certain cells, *Journal of Biological Chemistry* 270 (1995) 6149–6155.
17. Ichikawa, Y., Lin, Y.-C., Damas, D. P., Shen, G.-J., Garcia-Junceda, E., Williams, M. A., Bayer, R., ketcham, C., Walker, L. E., Paulson, J. C. & Wong, C.-H., Chemical-enzymatic synthesis and conformational analysis of sialyl Lewis X and derivatives. *Journal of the American Chemical Society*, 114 (1992) 9283–9298.
18. Smith P. L., Lowe J. B., Molecular cloning of a murine N-acetylgalactosamine transferase cDNA that determines expression of the T lymphocyte-specific CT oligosaccharide differentiation antigen, *Journal of Biological Chemistry*, 269 (1994) 15162–15171.
19. Hodgson, J., Carbohydrate-based therapeutics. *Bio/Technology*, 9 (1991) 609–613.
20. Yuen, C. T., Bezouska, K., O'Brien, J., Stoll, M., Lemoine, R., Lubineau, A., Kiso, M., Hasegawa, A., Bockovitch, N. J., Nicolaou, K. C. & Feizi, T., Sulfated blood group Lewis$^a$. A superior oligosaccharide ligand for human E-selectin. *Journal of Biological Chemistry*, 269 (1994) 1595–1598.
21. Neeser, J.-R. & Schweizer, T. F., A quantitative determination by capillary gas-liquid chromatography of neutral and amino-sugars (as O-methyloxime acetates), and a study on hydrolytic conditions for glycoproteins and polysaccharides in order to increase sugar recoveries. *Analytical Biochemistry*, 142 (1984) 58–67.

We claim:

1. A purified branched natural soluble polysaccharide consisting of a main chain having two or more side chains, wherein said side chains consist only of lactose units or units of the formula

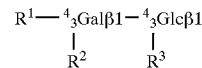

wherein Gal=galactose, Glc=glucose, $R^1$=hydrogen or N-acetylgalactosamine, $R^2$=hydrogen, N-acetylneuraminic acid or $HSO_3$, $R^3$=hydrogen or fucose.

2. The branched polysaccharide according to claim 1, which has the structure of the following formula:

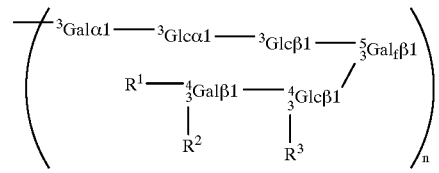

wherein n>1, Gal=galactose, Glc=glucose, $R^1$=hydrogen or N-acetylgalactosamine, $R^2$=hydrogen, N-acetylneuraminic acid or $HSO_3$, $R^3$=hydrogen or fucose, subscript "f" denotes a furanose form.

3. The polysaccharide according to claim 2, wherein each of $R^1$, $R^2$, and $R^3$ is hydrogen, and which polysaccharide comprises glucose and galactose in the molecular ratio 1:1.1.

4. A food composition comprising: a purified branched polysaccharide consisting of a main chain having two or more side chains, wherein said side chains consist only of lactose units or units of the formula

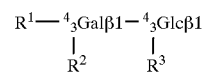

wherein Gal=galactose, Glc=glucose, $R^1$=hydrogen or N-acetylgalactosamine, $R^2$=hydrogen, N-acetylneuraminic acid or $HSO_3$, $R^3$=hydrogen or fucose; and an appropriate edible carrier.

5. The food composition according to claim 4, wherein said branched polysaccharide has the structure of the following formula:

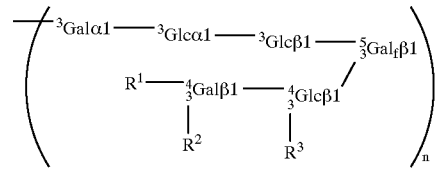

wherein n>1, Gal=galactose, Glc=glucose, $R^1$=hydrogen or N-acetylgalactosamine, $R^2$=hydrogen, N-acetylneuraminic acid or $HSO_3$, $R^3$=hydrogen or fucose, subscript "f" denotes a furanose form; and an appropriate edible carrier.

6. A cosmetic composition comprising: a purified branched polysaccharide consisting of a main chain having two or more side chains, wherein said side chains consist only of lactose units or units of the formula

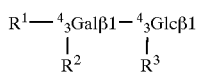

wherein Gal=galactose, Glc=glucose, $R^1$=hydrogen or N-acetylgalactosamine $R^2$=hydrogen, N-acetyineuraminic acid or $HSO_3$, $R^3$=hydrogen or fucose; and a cosmetically acceptable carrier.

7. The cosmetic composition according to claim 6, wherein said branched polysaccharide having the structure of the following formula:

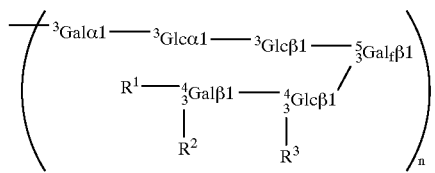

wherein n>1, Gal=galactose, Glc=glucose, $R^1$=hydrogen or N-acetylgalactosamine, $R^2$=hydrogen, N-acetylneuraminic acid or $HSO_3$, $R^3$=hydrogen or fucose, subscript "f" denotes a furanose form; and a cosmetically acceptable carrier.

8. The cosmetic composition according to claim 6, wherein said composition is selected from the group consisting of mouth rinse, toothpaste, tooth gel, chewing gum, cream, ointment, and balsam.

9. A pharmaceutical composition comprising: a purified branched polysaccharide consisting of a main chain having two or more side chains, wherein said side chains consist only of lactose units or units of the formula

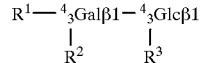

wherein Gal=palactose, Glc=glucose, $R^1$=hydrogen or N-acetylgalactosamine, $R^2$=hydrogen, N-acetylneuraminic acid or $HSO_3$, $R^3$=hydrogen or fucose; and a pharmaceutically acceptable carrier.

10. The pharmaceutical composition according to claim 9, wherein said composition is selected from the group consisting of a capsule, syrup, powder, and a tablet.

11. The pharmaceutical composition according to claim 9, wherein said branched polysaccharide having the structure of the following formula:

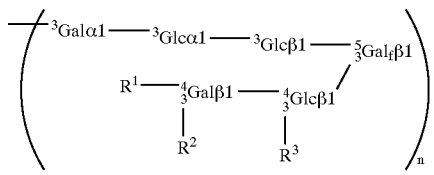

wherein n>1, Gal=galactose, Glc=glucose, $R^1$=hydrogen or N-acetylgalactosamine, $R^2$=hydrogen, N-acetyineuraminic acid or $HSO_3$, $R^3$ =hydrogen or fucose, subscript "f" denotes a furanose form; and a pharmaceutically acceptable carrier.

* * * * *